United States Patent
Noda et al.

(10) Patent No.: US 11,106,132 B2
(45) Date of Patent: Aug. 31, 2021

(54) ENERGY-SENSITIVE COMPOSITION, CURED PRODUCT, AND PATTERN FORMING METHOD

(71) Applicants: TOKYO OHKA KOGYO CO., LTD., Kawasaki (JP); Tokyo University of Science Foundation, Tokyo (JP)

(72) Inventors: Kunihiro Noda, Kawasaki (JP); Dai Shiota, Kawasaki (JP); Koji Arimitsu, Tokyo (JP)

(73) Assignees: Tokyo Ohka Kogyo Co., Ltd., Kawasaki (JP); Tokyo University of Science Foundation, Tokyo (JP)

( * ) Notice: Subject to any disclaimer, the term of this patent is extended or adjusted under 35 U.S.C. 154(b) by 80 days.

(21) Appl. No.: 16/390,429

(22) Filed: Apr. 22, 2019

(65) Prior Publication Data

US 2019/0332010 A1    Oct. 31, 2019

(30) Foreign Application Priority Data

Apr. 27, 2018   (JP) .............................. JP2018-086838

(51) Int. Cl.
| | | |
|---|---|---|
| *G03F 7/004* | (2006.01) | |
| *C08G 77/12* | (2006.01) | |
| *C07C 257/10* | (2006.01) | |
| *C07F 9/22* | (2006.01) | |

(52) U.S. Cl.
CPC .......... *G03F 7/0045* (2013.01); *C07C 257/10* (2013.01); *C07F 9/222* (2013.01); *C08G 77/12* (2013.01)

(58) Field of Classification Search
CPC ......... G03F 7/0045; G03F 7/075; C07F 9/065
See application file for complete search history.

(56) References Cited

U.S. PATENT DOCUMENTS

| | | | | |
|---|---|---|---|---|
| 6,174,982 B1* | 1/2001 | Nishida | .............. | C08G 77/60 528/10 |
| 2003/0036015 A1* | 2/2003 | Fedynyshyn | ......... | G03F 7/0045 430/270.1 |
| 2004/0259029 A1* | 12/2004 | Nagahara | .............. | G03F 7/0045 430/270.1 |
| 2016/0122292 A1 | 5/2016 | Sakai et al. | | |
| 2017/0184964 A1* | 6/2017 | Hatakeyama | ........... | G03F 7/168 |
| 2018/0187010 A1 | 7/2018 | Chisaka et al. | | |

FOREIGN PATENT DOCUMENTS

| | | |
|---|---|---|
| WO | WO 2014/208632 A1 | 12/2014 |
| WO | WO 2017/007010 A1 | 1/2017 |

OTHER PUBLICATIONS

English Machine Translation of Chisaka WO-2017/007010-A1 (Jan. 2017) (Year: 2017).*

* cited by examiner

*Primary Examiner* — John A McPherson
*Assistant Examiner* — Nicholas E Brown
(74) *Attorney, Agent, or Firm* — Knobbe Martens Olson & Bear LLP

(57) ABSTRACT

An energy-sensitive composition including at least one of a silane compound monomer capable of forming a polysilane compound, a silane compound oligomer and the polysilane compound, and a base generator (B) represented by the following formula (1):

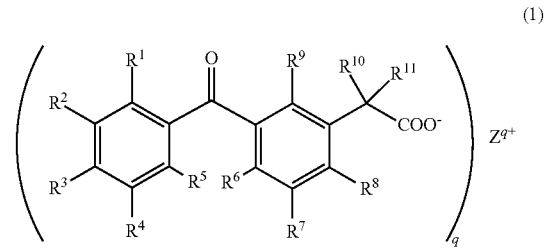

(1)

in which $R^1$ to $R^{11}$ each independently represents a hydrogen atom, a halogen atom, a nitro group, an alkyl group, an aryl group, an arylalkyl group or an alkoxy group, $R^5$ and $R^6$ may be connected to each other via a single bond or a divalent linking group, $Z^{q+}$ represents a q-valent counter cation composed of a base having a pKa of 24 or more, and q represents an integer of 1 or more.

10 Claims, No Drawings

ENERGY-SENSITIVE COMPOSITION, CURED PRODUCT, AND PATTERN FORMING METHOD

This application claims priority to Japanese Patent Application No. 2018-086838, filed Apr. 27, 2018, the entire content of which is incorporated herein by reference.

BACKGROUND OF THE INVENTION

Field of the Invention

The present invention relates to an energy-sensitive composition having excellent curability, a cured product of the composition, and a pattern forming method using the composition.

Related Art

Polysilane compounds having a silicon-silicon bond have been used in applications, for example, ceramics precursors, optoelectronic materials (for example, optoelectronic photographic materials such as photoresists and organic photoreceptors, optical transmission materials such as optical waveguides, optical recording materials such as optical memories, materials for electroluminescence elements), interlayer insulating films in various elements, sealing materials of light-emitting elements such as LED elements and organic EL elements, coating film for diffusion of impurities to semiconductor substrates, gap filling materials for semiconductor process and the like.

For example, Patent Document 1 discloses a composition including a polysilane compound. There is still room for improvement in curability and patterning of the composition including a polysilane compound, and there is a need to develop a curing agent which is satisfactory for curing the composition including a polysilane compound. Meanwhile, a photo base generator had room for improvement in quantum yield, storage stability of a composition including the photo base generator and the like, and there has been development of a photo base generator in which the quantum yield has been improved by having a specific structure (for example, Patent Document 2).

Patent Document 1: No. WO2017/007010A1
Patent Document 2: No. WO2014/208632A1

SUMMARY OF THE INVENTION

In light of the above problems of the prior art, an object of the present invention is to provide an energy-sensitive composition having excellent curability, a cured product of the composition, and a pattern forming method using the composition.

The present inventors have found that an energy-sensitive composition including a polysilane-based compound, and a base generator including a counter cation composed of a base having a pKa of 24 or more and an anion having a specific structure has excellent curability, thus completing the present invention.

A first aspect of the present invention is an energy-sensitive composition including at least one silane compound (A) selected from the group consisting of a silane compound monomer capable of forming a polysilane compound, a silane compound oligomer and the polysilane compound, and a base generator (B) represented by the following formula (1):

[Chem. 1]

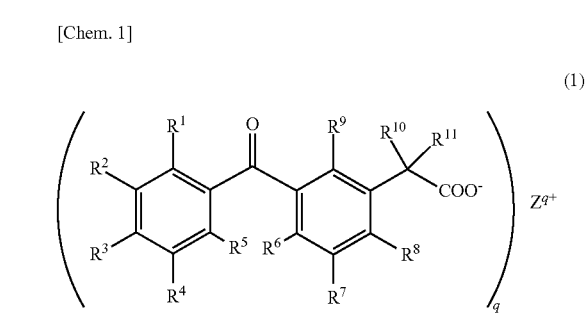

wherein, in the above formula, $R^1$ to $R^{11}$ each independently represent a hydrogen atom, a halogen atom, a nitro group, an alkyl group, an aryl group, an arylalkyl group or an alkoxy group, $R^5$ and $R^6$ may be connected to each other via a single bond or a divalent linking group, $Z^{q+}$ represents a q-valent counter cation composed of a base having a pKa of 24 or more, and q represents an integer of 1 or more.

A second aspect of the present invention is a cured product of the energy-sensitive composition according to the first aspect.

A third aspect of the present invention is a pattern forming method including applying the energy-sensitive composition according to the first aspect onto a substrate to form a film, and exposing the film.

The energy-sensitive composition according to the first aspect is excellent in curability and is particularly excellent in residual film properties of a cured product. The energy-sensitive composition according to the first aspect is excellent in contrast (for example, contrast between the exposed portions and the unexposed portions during exposure) during patterning. According to the present invention, it is possible to provide a cured product of the composition, and a pattern forming method using the composition.

DETAILED DESCRIPTION OF THE INVENTION

Embodiments of the present invention will be described in detail below, but the present invention is not limited to the following embodiments and can be implemented by appropriately introducing variations within the object of the present invention.

"To" as used herein means a range between the lower limit and the upper limit inclusive, unless otherwise specified.

<<Energy-Sensitive Composition>>

The energy-sensitive composition according to the first aspect includes at least one silane compound (A) selected from the group consisting of a silane compound monomer capable of forming a polysilane compound, a silane compound oligomer and the polysilane compound, and a base generator (B) represented by the following formula (1):

[Chem. 2]

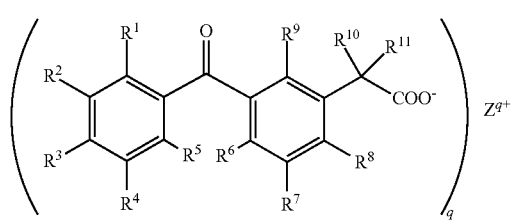

(1)

wherein, in the above formula, $R^1$ to $R^{11}$ each independently represent a hydrogen atom, a halogen atom, a nitro group, an alkyl group, an aryl group, an arylalkyl group or an alkoxy group, $R^5$ and $R^6$ may be connected to each other via a single bond or a divalent linking group, $Z^{q+}$ represents a q-valent counter cation composed of a base having a pKa of 24 or more, and q represents an integer of 1 or more.

The base generator (B) represented by the above formula (1) is capable of generating a base by being decomposed (for example, decarboxylation reaction) by light or heat (preferably light). The above-mentioned at least one silane compound (A) can be cured since a polymerization reaction, an increase in molecular weight and the like can proceed by an action of the base thus generated.

In the base generator represented by the above formula (1), an enol tautomer having an anion moiety shown in the following scheme can exist. The base generator according to the first aspect also includes a compound in which the anion moiety is the following enol tautomer.

[Chem. 3]

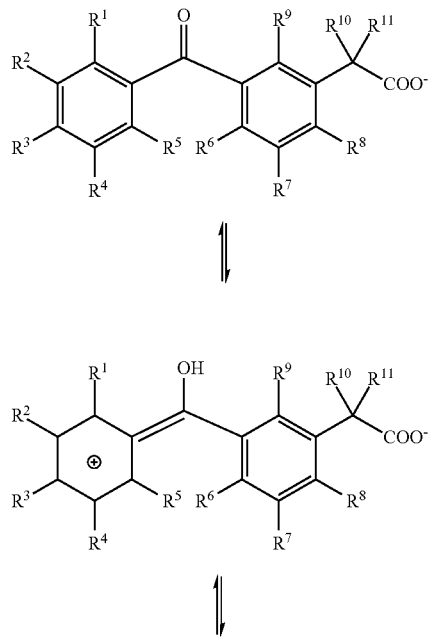

-continued

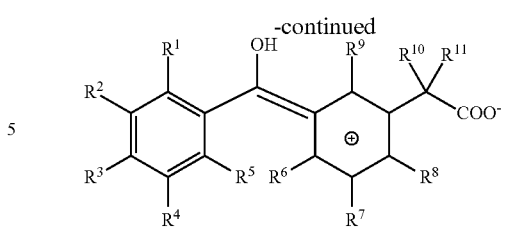

The respective components will be described below.

<At Least One Silane Compound (A) Selected from the Group Consisting of Silane Compound Monomer Capable of Forming Polysilane Compound, Silane Compound Oligomer and Polysilane Compound>

[Silane Compound Monomer Capable of Forming Polysilane Compound]

The above silane compound monomer is preferably a compound represented by the following formula (a):

$$X_{n1}SiR_{4-n1} \qquad (a)$$

wherein n1 is an integer of 2 or more and 4 or less, n1X(s) are each independently a halogen atom, and (4−n1)R(s) are each independently a hydrogen atom, a hydroxyl group, an organic group or a silyl group.

Examples of the halogen atom represented by X include a fluorine atom, a chlorine atom, a bromine atom or an iodine atom, and the halogen atom is preferably a chlorine atom or a bromine atom, and more preferably a chlorine atom.

Examples of the organic group represented by R include alkyl groups [alkyl groups having 1 or more and 10 or less carbon atoms, such as a methyl group, an ethyl group, a propyl group, an isopropyl group, a butyl group and a t-butyl group (preferably alkyl groups having 1 or more and 6 or less carbon atoms, and particularly alkyl groups having 1 or more and 4 or less carbon atoms, etc.)], cycloalkyl groups (cycloalkyl groups having 5 or more and 8 or less carbon atoms, such as a cyclohexyl group, and particularly cycloalkyl groups having 5 or 6 carbon atoms), alkenyl groups [alkenyl groups having 2 or more and 10 or less carbon atoms, such as an ethenyl group, a propenyl group and a butenyl group (preferably alkenyl groups having 2 or more and 6 or less carbon atoms, and particularly alkenyl groups having 2 or more and 4 or less carbon atoms, etc.)], cycloalkenyl groups [cycloalkenyl groups having 5 or more and 10 or less carbon atoms, such as a 1-cyclopentenyl group and a 1-cyclohexenyl group (preferably cycloalkenyl groups having 5 or more and 8 or less carbon atoms, and particularly cycloalkenyl groups having 5 or more and 7 or less carbon atoms, etc.)], aryl groups (aryl groups having 6 or more and 10 or less carbon atoms, such as a phenyl group and a naphthyl group), aryloxy groups (aryloxy groups having 6 or more and 10 or less carbon atoms, such as a phenoxy group and a naphthoxy group), aralkyl groups [alkyl groups having 1 or more and 6 or less carbon atoms which have an aryl group having 6 or more and 10 or less carbon atoms, such as a benzyl group and a phenethyl group (alkyl groups having 1 or more and 4 or less carbon atoms which have an aryl group having 6 or more and 10 or less carbon atoms, etc.)], amino groups, N-substituted amino groups (N-mono- or di-substituted amino groups substituted with the alkyl group, the cycloalkyl group, the aryl group, the aralkyl group, the acyl group and the like) and the like.

The alkyl group, the cycloalkyl group, the aryl group, or the aryl group constituting the aralkyl group may have one or plural substituents. Examples of such substituent include the above-exemplified alkyl groups (particularly alkyl groups having 1 or more and 6 or less carbon atoms) and the like. Examples of the organic group having such substituent include aryl groups having 6 or more and 10 or less carbon atoms which have an alkyl group having 1 or more and 6 or less carbon atoms, such as a tolyl group (methylphenyl group), a xylenyl group (dimethylphenyl group), an ethylphenyl group and a methylnaphthyl group (preferably aryl groups having 6 or more and 10 or less carbon atoms which have one or more and three or less alkyl group having 1 or more and 4 or less carbon atoms, and particularly phenyl groups which have one or two alkyl groups having 1 or more and 4 or less carbon atoms, etc.) and the like.

Examples of the silyl group include substituted silyl groups substituted with the alkyl group, the cycloalkyl group, the alkenyl group, the cycloalkenyl group, the aryl group, the aralkyl group and the alkoxy group and the like.

When n1 is 2 (dihalosilane compound monomer), R is preferably a hydrocarbon group such as an alkyl group or an aryl group. At least one of R may be an aryl group.

Examples of typical dihalosilane compound include dialkyldihalosilane (di $C_{1-10}$ alkyldihalosilane such as dimethyldichlorosilane, preferably di $C_{1-6}$ alkyldihalosilane, and more preferably di $C_{1-4}$ alkyldihalosilane, etc.), monoalkylmonoaryldihalosilane (mono $C_{1-10}$ alkylmono $C_{6-12}$ aryldihalosilane such as methylphenyldichlorosilane, preferably mono $C_{1-6}$ alkylmono $C_{6-10}$ aryldihalosilane, and more preferably mono $C_{1-4}$ alkylmono $C_{6-8}$ aryldihalosilane, etc.), diaryldihalosilane (di $C_{6-12}$ aryldihalosilane such as diphenyldichlorosilane, preferably di $C_{6-10}$ aryldihalosilane, and more preferably di $C_{6-8}$ aryldihalosilane, etc.), monoalkylmonoaryloxydihalosilane (mono $C_{1-10}$ alkylmono $C_{6-12}$ aryloxydihalosilane such as methylphenoxydichlorosilane, preferably mono $C_{1-6}$ alkylmono $C_{6-10}$ aryloxydihalosilane, and more preferably mono $C_{1-4}$ alkylmono $C_{6-8}$ aryloxydihalosilane, etc.), diaryloxydihalosilane (di $C_{6-12}$ aryloxydihalosilane such as diphenoxydichlorosilane, preferably di $C_{6-10}$ aryloxydihalosilane, and more preferably di $C_{6-8}$ aryloxydihalosilane, etc.) and the like. The dihalosilane compound is preferably dialkyldihalosilane or monoalkylmonoaryldihalosilane. The dihalosilane compound can be used alone or in combination of two or more.

When n1 is 3 (trihalosilane compound monomer), R is preferably a hydrocarbon group such as an alkyl group, a cycloalkyl group, an optionally substituted aryl group or an aralkyl group, particularly preferably an alkyl group or an aryl group, and more preferably an aryl group.

Examples of typical trihalosilane compound include alkyltrihalosilane ($C_{1-10}$ alkyltrihalosilane such as methyltrichlorosilane, butyltrichlorosilane, t-butyltrichlorosilane or hexyltrichlorosilane, preferably $C_{1-6}$ alkyltrihalosilane, and more preferably $C_{1-4}$ alkyltrihalosilane, etc.), cycloalkyltrihalosilane (mono $C_{6-10}$ cycloalkyltrihalosilane such as cyclohexyltrihalosilane), aryltrihalosilane ($C_{6-12}$ aryltrihalosilane such as phenyltrichlorosilane, tolyltrichlorosilane or xylyltrichlorosilane, preferably $C_{6-10}$ aryltrihalosilane, and more preferably $C_{6-8}$ aryltrihalosilane, etc.), aryloxytrihalosilane ($C_{6-12}$ aryloxytrihalosilane such as phenoxytrichlorosilane, tolyloxytrichlorosilane or xylyloxytrichlorosilane, preferably $C_{6-10}$ aryloxytrihalosilane, and more preferably $C_{6-8}$ aryloxytrihalosilane, etc.) and the like. The trihalosilane compound is preferably alkyltrihalosilane or aryltrihalosilane. The trihalosilane compound can be used alone or in combination of two or more.

Specific examples in which n1 is 4 (tetrahalosilane compound monomer) include tetrachlorosilane, dibromodichlorosilane, tetrabromosilane and the like. The tetrahalosilane compound may be used alone or in combination of two or more. The tetrahalosilane compound is preferably used in combination with a mono-, di- or tri-halosilane compound.

The halosilane compound may also be a monosilane compound. Examples of typical monohalosilane include trialkylmonohalosilane (tri $C_{1-10}$ alkylmonohalosilane such as trimethylchlorosilane, preferably tri $C_{1-6}$ alkylmonohalosilane, and more preferably tri $C_{1-4}$ alkylmonohalosilane, etc.), dialkylmonoarylmonohalosilane (di $C_{1-10}$ alkylmono $C_{6-12}$ arylmonohalosilane such as dimethylphenylchlorosilane, preferably di $C_{1-6}$ alkylmono $C_{6-10}$ arylmonohalosilane, and more preferably di $C_{1-4}$ alkylmono $C_{6-8}$ arylmonohalosilane, etc.), monoalkyldiarylmonohalosilane (mono $C_{1-10}$ alkyldi $C_{6-12}$ arylmonohalosilane such as methyldiphenylchlorosilane, preferably mono $C_{1-6}$ alkyldi $C_{6-10}$ arylmonohalosilane, and more preferably mono $C_{1-4}$ alkyldi $C_{6-8}$ arylmonohalosilane, etc.), triarylmonohalosilane (tri $C_{6-12}$ arylmonohalosilane such as triphenylchlorosilane, preferably tri $C_{6-10}$ arylmonohalosilane, more preferably tri $C_{6-8}$ arylmonohalosilane, and etc.), dialkylmonoaryloxymonohalosilane (di $C_{1-10}$ alkylmono $C_{6-12}$ aryloxymonohalosilane such as dimethylphenoxychlorosilane, preferably di $C_{1-6}$ alkylmono $C_{6-10}$ aryloxymonohalosilane, and more preferably di $C_{1-4}$ alkylmono $C_{6-8}$ aryloxymonohalosilane, etc.), monoalkyldiaryloxymonohalosilane (mono $C_{1-10}$ alkyldi $C_{6-12}$ aryloxymonohalosilane such as methyldiphenoxychlorosilane, preferably mono $C_{1-6}$ alkyldi $C_{6-10}$ aryloxymonohalosilane, and more preferably mono $C_{1-4}$ alkyldi $C_{6-8}$ aryloxymonohalosilane, etc.), triaryloxymonohalosilane (tri $C_{6-12}$ aryloxymonohalosilane such as triphenoxychlorosilane, preferably tri $C_{6-10}$ aryloxymonohalosilane, and more preferably tri $C_{6-8}$ aryloxymonohalosilane, etc.) and the like. The monohalosilane compound can be used alone or in combination of two or more.

These silane compound monomers can be used alone or in combination of two or more.

The silane compound monomer preferably includes at least one selected from a dihalosilane compound monomer and a trihalosilane compound monomer.

When the silane compound monomer includes a trihalosilane compound monomer and/or a tetrahalosilane compound monomer, it is possible to produce a network (network or branched) polysilane compound. In the case of obtaining a network polysilane compound, examples of typical halosilane monomer (or a combination thereof) include (a) alkyltrihalosilane (for example, alkyltrihalosilane alone, a combination of methyltrihalosilane with $C_{2-10}$ alkyltrihalosilane, $C_{2-10}$ alkyltrihalosilane, etc.), (b) aryltrihalosilane (for example, aryltrihalosilane alone), (c) a combination of aryltrihalosilane with dihalosilane (for example, monoalkylmonoaryldihalosilane, etc.) and the like.

In the halosilane compound, a ratio (use ratio) of at least one selected from a dihalosilane compound monomer and a trihalosilane compound monomer may be 50 mol % or more (for example, 60 mol % or more), preferably 70 mol % or more (for example, 80 mol % or more), and more preferably 90 mol % (for example, 95 mol % or more), based on the entire silane compound monomer.

In the case of obtaining a network polysilane, a ratio (use ratio) of the trihalosilane compound monomer may be 30 mol % or more (for example, 40 mol % or more), preferably 50 mol % or more (for example, 60 mol % or more), more preferably 70 mol % or more (for example, 75 mol % or more), and particularly 80 mol % or more, based on the entire silane compound monomer.

In the case of using the dihalosilane compound monomer in combination with the trihalosilane compound monomer, the ratio (dihalosilane compound monomer/trihalosilane compound monomer) (molar ratio) may be 99/1 to 1/99, preferably 90/10 to 2/98 (for example, 85/15 to 2/98), more preferably 80/20 to 3/97 (for example, 70/30 to 4/96), particularly 60/40 to 5/95 (for example, 50/50 to 7/93), usually 50/50 to 5/95 (for example, 45/55 to 7/93, preferably 40/60 to 10/90, and more preferably 30/70 to 88/12).

The halosilane compound monomer preferably has a purity as high as possible. For example, a liquid halosilane compound is preferably used after drying with calcium hydride as a desiccant followed by distillation, and a solid halosilane compound is preferably used after purifying by a recrystallization method.

[Silane Compound Oligomer Capable of Forming Polysilane Compound]

Examples of the silane compound oligomer include an oligomer in which at least two silane compound monomers are polymerized by any method, and the silane compound oligomer is preferably an oligomer in which two or more and twenty or less silane compound monomers are polymerized, more preferably an oligomer in which three or more and ten or less silane compound monomers are polymerized, still more preferably an oligomer in which four or more and nine or less silane compound monomers are polymerized, and particularly preferably an oligomer in which five or more and eight or less silane compound monomers are polymerized.

A mass average molecular weight (Mw) of the silane compound oligomer is not particularly limited as long as it does not interfere with the object of the present invention, and is preferably 200 or more and 2,000 or less, more preferably 300 or more and 1,000 or less, still more preferably 400 or more and 900 or less, and particularly preferably 500 or more and 800 or less, in terms of polystyrene. Silane compound oligomers having different mass average molecular weights may be used in combination of two or more.

Examples of the method for producing the above silane compound oligomer include (a) a method in which the above silane compound monomer is subjected to dehalogenation polycondensation using magnesium as a reducing agent ("magnesium reduction method", methods mentioned in No. WO98/29476A1 and Japanese Unexamined Patent Application, Publication No. 2003-277507, etc.), (b) a method in which dialkyldihalosilane or dihalotetraalkyldisilane in a toluene solvent is reductively coupled with vigorous stirring at a temperature of 100° C. or higher using alkali metal such as metallic sodium [J. Am. Chem. Soc., 103(1981)7352], (c) a method in which disilane masked with biphenyl is subjected to anionic polymerization (Japanese Unexamined Patent Application, Publication No. 1-23063), (d) a method in which cyclic silanes are subjected to ring-opening polymerization (Japanese Unexamined Patent Application, Publication No. 5-170913), (e) a method in which hydrosilanes are subjected to dehydrogenation polycondensation by a transition metal complex catalyst (Japanese Examined Patent Application, Publication No. 7-17753), (f) a method in which dihalosilanes are electroreduced at a temperature of room temperature or lower to produce polysilane (Japanese Unexamined Patent Application, Publication No. 7-309953) and the like, and the magnesium reduction method is preferable. The silane compound oligomer can be used alone or in combination of two or more.

[Polysilane Compound]

There is no particular limitation on the structure of the polysilane compound. The polysilane compound may be linear, branched, network or cyclic, and preferably has a linear or branched chain structure. The polysilane compound may have a silanol group, or an alkoxy group bonded to a silicon atom. Examples of the polysilane compound include a polysilane compound having 6 or more and 40 or less Si atoms, and the polysilane compound is preferably a polysilane compound having 10 or more and 30 or less Si atoms. The polysilane compound preferably includes at least one of polysilane structures represented by the following general formula (A1), and more preferably a polysilane structure represented by the following general formula (A1-1):

[Chem. 4]

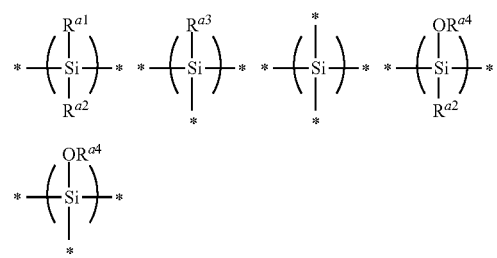

(A1)

wherein, in the above general formula (A1), $R^{a1}$, $R^{a2}$ and $R^{a3}$ each independently represent a hydrogen atom, a hydroxyl group or an organic group, $R^{a4}$ each independently represent an alkyl group or an aryl group, and

* represents a bond, and

[Chem. 5]

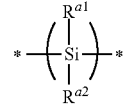

(A1-1)

wherein, in the above general formula (A1-1), *, $R^{a1}$ and $R^{a2}$ are the same as defined in the general formula (A1). Specific examples and preferred examples of the organic group represented by $R^{a1}$ to $R^{a3}$ are the same as those mentioned above as specific examples and preferred examples of the organic group represented by R. Examples of the alkyl group of $R^{a4}$ include alkyl groups having 1 or more and 6 or less carbon atoms, and the alkyl group is preferably an alkyl group having 1 or more and 4 or less carbon atoms, and more preferably a methyl group or an ethyl group. Examples of the aryl group of $R^{a4}$ include aryl groups having 6 or more and 10 or less carbon atoms, and the aryl group is preferably a phenyl group or a naphthyl group. The polysilane compound is preferably at least one selected from the group consisting of polysilane compounds represented by the following general formulas (A-2-1) and (A-2-2):

$$(R^{a21}R^{a22}R^{a23}Si)_{a1}(R^{a24}R^{a25}Si)_{a2}(R^{a26}Si)_{a3}(Si)_{a4} \quad (A\text{-}2\text{-}1)$$

wherein, in the above general formula, $R^{a21}$, $R^{a22}$, $R^{a23}$, $R^{a24}$, $R^{a25}$ and $R^{a26}$ each independently represent a hydrogen atom, a hydroxyl group or an organic group, a1, a2, a3 and a4 each independently represent a molar fraction, a1+a2+a3+a4=1, 0≤a1≤1, 0≤a2≤1, 0≤a3≤1 and 0≤a4≤1; and

[Chem. 6]

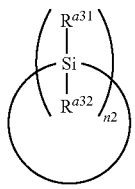

(A-2-2)

wherein, in the above general formula (A-2-2), $R^{a31}$ and $R^{a32}$ each independently represent a hydrogen atom, a hydroxyl group or an organic group, and n2 represents an integer of 3 or more and 20 or less. Examples of the organic group represented by $R^{a21}$ to $R^{a26}$ and $R^{a31}$ and $R^{a32}$ include those which are the same as specific examples and preferred examples mentioned above as the organic group represented by R. It is possible to introduce, as the organic group represented by $R^{a21}$ to $R^{a26}$ and $R^{a31}$ and $R^{a32}$, for example, any organic group by the method mentioned in Japanese Unexamined Patent Application, Publication No. 2003-261681, paragraph 0031.

It is possible to prepare the above polysilane compound by applying various methods for producing the polysilane. Examples of the method include (a) a method in which the above silane compound monomer is subjected to dehalogenation polycondensation using magnesium as a reducing agent ("magnesium reduction method", methods mentioned in No. WO98/29476A1 and Japanese Unexamined Patent Application, Publication No. 2003-277507, etc.), (b) a method in which dialkyldihalosilane or dihalotetraalkyldisilane in a toluene solvent is reductively coupled by vigorous stirring at a temperature of 100° C. or higher using alkali metal such as metallic sodium [J. Am. Chem. Soc., 103 (1981)7352], (c) a method in which diasilene masked with biphenyl is subjected to anionic polymerization (Japanese Unexamined Patent Application, Publication No. 1-23063), (d) a method in which cyclic silanes are subjected to ring-opening polymerization (Japanese Unexamined Patent Application, Publication No. 5-170913), (e) a method in which hydrosilanes are subjected to dehydrogenation polycondensation by a transition metal complex catalyst (Japanese Examined Patent Application, Publication No. 7-17753), (f) a method in which dihalosilanes are electroreduced at a temperature of room temperature or lower to produce polysilane (Japanese Unexamined Patent Application, Publication No. 7-309953) and the like, and the magnesium reduction method is preferable.

It is also possible to use, as the polysilane compound, commercially available products such as OGSOL SI-10-10 (polymethylphenylsilane), SI-10-20 (polymethylphenylsilane), SI-20-10 (polyphenylsilane), SI-20-10 (revised) (polyphenylsilane), and SI-30-10 (cyclic polydiphenylsilane) manufactured by OSAKA GAS CHEMICALS CO. LTD. It is also possible to use those obtained by lowering the molecular weight of these commercially available products under the following basic conditions.

A mass average molecular weight (Mw) of the polysilane compound is not particularly limited as long as it does not interfere with the object of the present invention, and is preferably 600 or more and 20,000 or less, more preferably 1,000 or more and 10,000 or less, and still more preferably 1,200 or more and 5,000 or less, in terms of polystyrene. Polysilane compounds having different mass average molecular weights may be used in combination of two or more.

The silane compound monomer, the silane compound oligomer and the polysilane compound may be used alone, respectively, and a mixture of at least two compounds selected from the group consisting of the silane compound monomer, the silane compound oligomer and the polysilane compound may also be used.

There is no particular limitation on the contents of the silane compound monomer, the silane compound oligomer and the polysilane compound in the above energy-sensitive composition. In view of film-forming properties, each content of the silane compound monomer, the silane compound oligomer and the polysilane compound (the total content when plural kinds of the silane compound monomer, the silane compound oligomer and the polysilane compound are included) is preferably 10% by mass or more and 99% by mass or less, more preferably 50% by mass or more and 98% by mass or less, and particularly preferably 60% by mass or more and 95% by mass or less, based on the mass of the entire composition (excluding a solvent).

The polysilane compound and a polysiloxane compound differ in function and properties and, for example, the polysiloxane compound has room for improvement in hydrophobicity and electrical insulation properties. It is preferable that a compound in which X in the above formula (a) is an alkoxy group is not included in the above silane compound monomer since the compound can form a polysiloxane compound. It is also preferable that a polysiloxane compound, which can be formed from a compound in which X in the above formula (a) is an alkoxy group, is not included in the polysilane compound according to the first aspect.

<Base Generator (B) Represented by Formula (1)>

Examples of the halogen atom of $R^1$ to $R^{11}$ include a fluorine atom, a chlorine atom, a bromine atom or an iodine atom, and the halogen atom is preferably a chlorine atom or a bromine atom. Examples of the alkyl group of $R^1$ to $R^{11}$ include alkyl groups which may have a substituent or not, and may be linear, branched or cyclic, and have 1 or more and 12 or less carbon atoms (preferably having 1 or more and 10 or less carbon atoms, and more preferably having 1 or more and 6 or less carbon atoms), and specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, a nonylbonyl group (norbornan-X-yl group), a bornyl group (bornan-X-yl group), a menthyl group (menth-X-yl group), an adamantyl group, a decahydronaphthyl group and the like.

Among the above-mentioned alkyl groups, for example, linear, branched or cyclic alkyl groups having 1 or more and 4 or less carbon atoms, such as a methyl group, an ethyl group, an n-propyl group, an isopropyl group, an n-butyl group, an isobutyl group, a sec-butyl group, a tert-butyl group and a cyclobutyl group are preferable, and alkyl groups having 1 carbon atom such as a methyl group are more preferable.

Examples of the aryl group of $R^1$ to $R^{11}$ include aryl groups which may be monocyclic or condensed polycyclic and may have a substituent or not, and have 6 or more and 14 or less carbon atoms, such as a phenyl group, a naphthyl group, an anthracenyl group (anthryl group) and a phenanthrenyl group (phenanthryl group). Among these aryl groups, for example, aryl group having 6 or more and 10 or less carbon atoms, such as a phenyl group and a naphthyl group are preferable, and aryl groups having 6 carbon atoms such as a phenyl group are more preferable.

Examples of the arylalkyl group of $R^1$ to $R^{11}$ include arylalkyl group which may have a substituent or not and may be monocyclic or condensed polycyclic, and have 7 or more and 15 or less carbon atoms, such as a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (anthrylmethyl group) and a phenanthrenylmethyl group (phenanthrylmethyl group). Among these arylalkyl groups, arylalkyl groups having 7 carbon atoms such as a benzyl group are preferable.

Examples of the alkoxy group of $R^1$ to $R^{11}$ include alkoxy groups which may have a substituent or not and may be linear, branched or cyclic, and have 1 or more and 12 or less carbon atoms (preferably having 1 or more and 6 or less carbon atoms, and more preferably having 1 or more and 4 or less carbon atoms) such as a methoxy group, an ethoxy group, an n-propoxy group, an isopropoxy group, an n-butoxy group, an isobutoxy group, a sec-butoxy group, a tert-butoxy group, a cyclobutoxy group, an n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, an n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, an n-heptyloxy group, an isoheptyloxy group, a sec-heptyloxy group, a tert-heptyloxy group, a neoheptyloxy group, a cycloheptyloxy group, an n-octyloxy group, an isooctyloxy group, a sec-octyloxy group, a tert-octyloxy group, a neooctyloxy group, a 2-ethylhexyloxy group, a cyclooctyloxy group, an n-nonyloxy group, an isononyloxy group, a sec-nonyloxy group, a tert-nonyloxy group, a neononyloxy group, a cyclononyloxy group, an n-decyloxy group, an isodecyloxy group, a sec-decyloxy group, a tert-decyloxy group, a neodecyloxy group, a cyclodecyloxy group, an n-undecyloxy group, a cycloundecyloxy group, an n-dodecyloxy group, a cyclododecyloxy group, a norbornyloxy group (bornan-X-yloxy group), a bornyloxy group (bornan-X-yloxy group), a menthyloxy group (menth-X-yloxy group), an adamantyloxy group and a decahydronaphthyloxy group. Among these alkoxy groups, for example, linear, branched or cyclic alkoxy groups having 1 or more and 4 or less carbon atoms, such as a methoxy group, an ethoxy group, an n-propoxy group, an isopropoxy group, an n-butoxy group, isobutoxy group, a sec-butoxy group, a tert-butoxy group and a cyclobutoxy group are preferable, and alkoxy groups having 1 carbon atom such as a methoxy group are more preferable.

$R^5$ and $R^6$ may be connected to each other via a single bond or a divalent linking group. Examples of the divalent linking group include an alkylene group, an oxygen atom or a sulfur atom, and the divalent linking group is preferably an oxygen atom. Examples of the alkylene group include linear or branched alkylene groups have 1 or more and 4 or less carbon atoms which may have a substituent or not, and specific examples thereof include a methylene group, an ethylene group, an isopropylene group and the like. $R^1$ to $R^{11}$ are preferably a hydrogen atom and an alkyl group having 1 or more and 12 or less carbon atoms, and more preferably a hydrogen atom. $R^5$ and $R^6$ are preferably connected to each other via a divalent linking group.

q is preferably an integer of 1 or more and 3 or less, more preferably an integer of 1 or 2, and still more preferably 1.

Preferred specific examples of the anion moiety will be exemplified below, but the present invention is not limited thereto.

[Chem. 7]

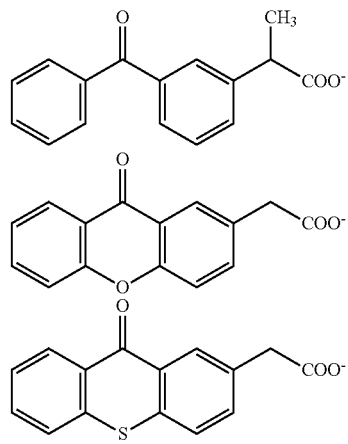

A q-valent counter cation $Z^{q+}$ is composed of a base having a pKa of 24 (pKa of conjugate acid) (preferably 25 or more, more preferably 28 or more, and still more preferably 30 or more). Thereby, a strong base is generated upon exposure, thus enabling the achievement of satisfactory curability, and preferably an improvement in contrast (contrast between the exposed portions and the unexposed portions) of patterning. The upper limit of pKa is not particularly limited and is, for example, 50 or less, preferably 45 or less, more preferably 40 or less, and particularly preferably 35 or less.

As used herein, "pKa" means a pKa in an acetonitrile ($CH_3CN$) solvent and is, for example, mentioned in Fourth Revision of Kagaku-Binran II (1993) edited by The Chemical Society of Japan, Maruzen Co., Ltd. The lower this value, the larger the acid strength. Regarding the pKa in $CH_3CN$, it is also possible to determine the value based on a database of Hammett's substituent constant and known literature values by calculation (J. Org. Chem. 2016, 81, 7349-7361).

The base having a pKa of 24 or more constituting the q-valent counter cation $Z^{q+}$ is not particularly limited as long as it has the pKa of 24 or more, and the base includes an organic base or an inorganic base, and is preferably an organic base.

From a viewpoint of basicity and nucleophilicity to a silicon atom, the base having a pKa of 24 or more preferably includes at least one base selected from the group consisting of a phosphazene compound and an amidine compound, namely, the above q-valent counter cation $Z^{q+}$ preferably includes at least one cation selected from the group consisting of a phosphazene compound cation and an amidine compound cation.

(Phosphazene Compound)

As used herein, "phosphazene compound" means "organic compound having a —P=N— bond in the molecule". The number of —P=N— bonds in the above phosphazene compound is not particularly limited as long as the pKa of 24 or more is achieved and includes 1 or more and 10 or less, and is preferably 1 or more and 6 or less, more preferably 1 or more and 5 or less, still more preferably 2 or more and 4 or less, particularly preferably 2 or 3, and most preferably 2. The phosphazene compound is preferably a compound in which at least two compounds represented by the following formula (b1) or structures represented by the following formula (b1) are connected to each other, and more preferably a compound in which at least two structures represented by the following formula (b1) are connected to each other:

[Chem. 8]

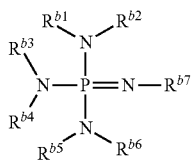

(b1)

wherein, in the above formula (b1), $R^{b1}$ to $R^{b7}$ each independently represent a monovalent organic group which may include a hydrogen or a hetero atom, and at least two of $R^{b1}$ to $R^{b7}$ may be bonded to each other to form a ring.

The monovalent organic group which may include a hetero atom of $R^{b1}$ to $R^{b7}$ preferably has 1 or more and 20 or less carbon atoms, more preferably 1 or more and 10 or less carbon atoms, and still more preferably 1 or more and 6 or less carbon atoms. Examples of the organic group include an alkyl group, an arylalkyl group and the like, which may include a hetero atom. The alkyl group which may include a hetero atom may be linear, branched or cyclic and examples thereof include alkyl groups having 1 or more and 12 or less carbon atoms (preferably having 1 or more and 10 or less carbon atoms, and more preferably having 1 or more and 6 or less carbon atoms), and specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, a nonylbonyl group (norbornan-X-yl group), a bornyl group (bornan-X-yl group), a menthyl group (menth-X-yl group), an adamantyl group, a decahydronaphthyl group and the like.

Among the above-mentioned alkyl groups, for example, linear, branched or cyclic alkyl groups having 1 or more and 4 or less carbon atoms such as a methyl group, an ethyl group, an n-propyl group, an isopropyl group, an n-butyl group, an isobutyl group, a sec-butyl group, a tert-butyl group and a cyclobutyl group are preferable.

Examples of the arylalkyl group which may have a hetero atom include arylalkyl groups having 7 or more and 15 or less carbon atoms, and specific examples thereof include a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (anthrylmethyl group), a phenanthrenylmethyl group (phenanthrylmethyl group) and the like. Among these arylalkyl groups, arylalkyl groups having 7 carbon atoms, such as a benzyl group are preferable.

Examples of the hetero atom which can be possessed by the monovalent organic group of $R^{b1}$ to $R^{b7}$ include a nitrogen atom, an oxygen atom, a phosphorus atom or a sulfur atom. It is preferable that the hetero atom is bonded to a carbon atom and does not constitute an acid functional group such as a carboxyl group or a sulfone group. It is preferable that $R^{b7}$ is not a hydrogen atom. Examples of the ring which can be formed by at least two of $R^{b1}$ to $R^{b7}$ include a five-membered ring, a six-membered ring or a seven-membered ring, and the ring is preferably a six-membered ring.

The compound in which at least two structures represented by the above formula (b1) are connected to each other is preferably a compound in which two or more and six or less structures represented by the above formula (b1) are connected to each other, more preferably a compound in which two or more and four or less structures represented by the above formula (b1) are connected to each other, and still more preferably a compound in which two or three structures represented by the above formula (b1) are connected to each other. The aspect in which at least two structures represented by the above formula (b1) are connected to each other is preferably an aspect in which one structure represented by the above formula (b1) and the other structure represented by the above formula (b1) are connected so as to share one nitrogen atom in the above formula (b1). A molecular weight (Mw) of the phosphazene compound is, for example, 120 to 900 and is preferably 250 to 600, and more preferably 300 to 500, from the viewpoint of curability or residual film properties.

Preferred specific examples of the phosphazene compound will be exemplified below, but the present invention is not limited thereto.

[Chem. 9]

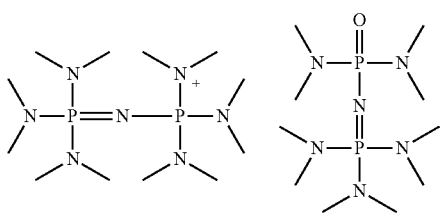

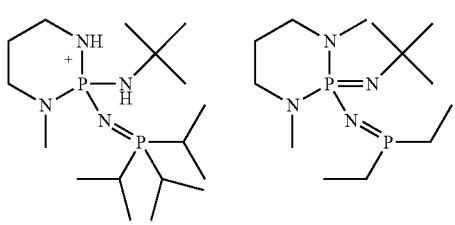

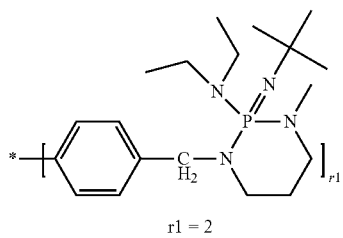

rl = 2

[Chem. 10]

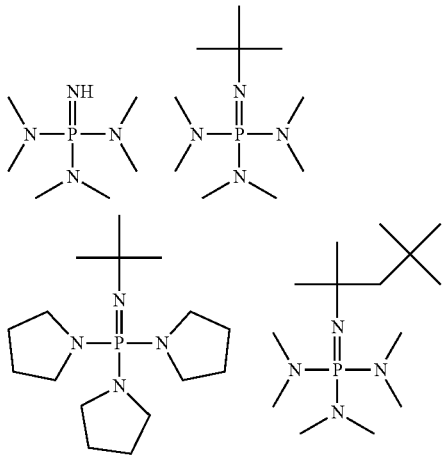

[Chem. 11]

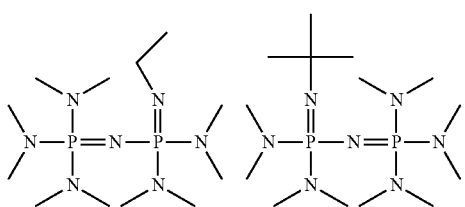

[Chem. 12]

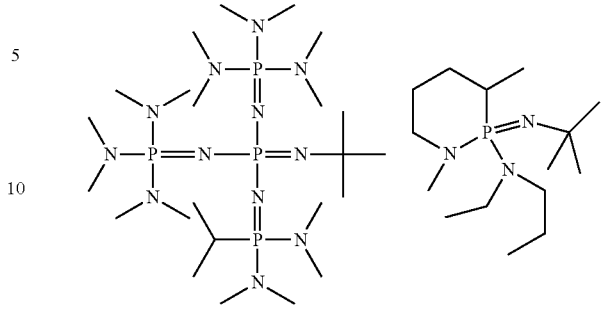

(Amidine Compound)

The amidine compound is preferably a compound represented by the following formula (b2):

[Chem. 13]

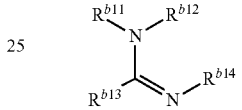

(b2)

wherein, in the above formula (b2), $R^{b11}$ to $R^{b14}$ each independently represent a monovalent organic group which may include a hydrogen or hetero atom, at least one of $R^{b11}$ to $R^{b14}$ represents a monovalent organic group which may include a hetero atom, and at least two of $R^{b11}$ to $R^{b14}$ may be bonded to each other to form a ring. Specific examples and preferred examples of the monovalent organic group which may include a hetero atom of $R^{b11}$ to $R^{b14}$ include those which are the same as mentioned above as the monovalent organic group which may include a hetero atom of $R^{b1}$ to $R^{b7}$. Examples of the hetero atom which can be possessed by the monovalent organic group of $R^{b11}$ to $R^{b14}$ include a nitrogen atom, an oxygen atom, a phosphorus atom or a sulfur atom. It is preferable that the hetero atom is bonded to a carbon atom and does not constitute an acid functional group such as a carboxyl group or a sulfone group. It is preferable that $R^{b14}$ is not a hydrogen atom. Examples of the ring which can be formed by at least two of $R^{b1}$ to $R^{b14}$ include a five-membered ring, a six-membered ring or a seven-membered ring, and the ring is preferably a six-membered ring or a seven-membered ring. Amidine including at least one ring structure (i.e., cyclic amidine) is preferable. Cyclic amidine including two ring structures (i.e., dicyclic amidine) is more preferable. The amidine compound is more preferably a compound represented by the following formula (b2-1):

[Chem. 14]

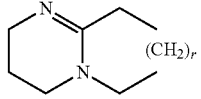

(b2-1)

wherein, in the above formula, r represents an integer of 1 or more and 3 or less.

Specific examples of the amidine compound include 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, 1-ethyl-2-isopropyl-1,4,5,6-tetrahydropyrimidine, DBU (i.e., 1,8-diazabicyclo[5.4.0]-7-undecene), DBN (i.e., 1,5-diazabicyclo[4.3.0]-5-nonene) and those analogous thereto, and combinations thereof. Examples of preferred amidine include 1,2-dimethyl-1,4,5,6-tetrahydropyrimidine, DBU (i.e., 1,8-diazabicyclo[5.4.0]-7-undecene), DBN (i.e., 1,5-diazabicyclo[4.3.0]-5-nonene) and combinations thereof. The amidine is more preferably DBU, DBN and a combination thereof, and most preferably DBU. The base generator (B) is composed of a cation moiety and an anion moiety as is apparent from the above formula (1), and a constitutional molar ratio of the cation moiety and the anion moiety, for example, cation moiety:anion moiety is in a range of 1:1 to 1:2, and preferably 1:1 to 1:1.5.

The base generator (B) in the energy-sensitive composition may be included alone or in combination of two or more. The content of the base generator (B) in the energy-sensitive composition is preferably 0.01% by mass or more and 40% by mass or less, more preferably 0.1% by mass or more and 20% by mass or less, and still more preferably 1% by mass or more and 10% by mass or less, based on the mass of the entire composition (excluding a solvent). The content of the base generator (B) in the energy-sensitive composition is, for example, 0.1 part by mass or more and 30 parts by mass or less, preferably 0.5 part by mass or more and 20 parts by mass or less, and more preferably 1 part by mass or more and 15 parts by mass or less, when the contents of the silane compound monomer, the silane compound oligomer and the polysilane compound are 100 parts by mass.

The base generator (B) can be produced by mixing an acid represented by the following formula (K) with the base having a pKa of 24 or more under optional conditions, followed by a reaction (for example, neutralization reaction).

<Acid>

The energy-sensitive composition according to the first aspect may further include an acid so as to improve the stability. From the viewpoint of the uniformity (compatibility, congeniality), the acid is preferably conjugate acid which is the anion moiety in a base generator represented by the above formula (1), and specifically an acid represented by the following formula (K):

[Chem. 15]

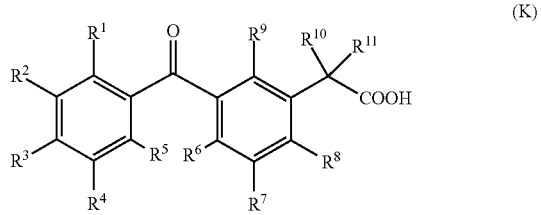

(K)

wherein, in the above formula, $R^1$ to $R^{11}$ are the same as $R^1$ to $R^{11}$ defined in the above formula (1).

Examples of the acid other than the conjugate acid include any organic acid or inorganic acid, and the acid is preferably an organic acid. Examples of the acid other than the conjugate acid include monovalent or divalent or higher multivalent organic acid having 1 or more and 30 or less carbon atoms, and specific examples thereof include formic acid, acetic acid, propionic acid, butanoic acid, pentanoic acid, hexanoic acid, heptanoic acid, octanoic acid, nonanoic acid, decanoic acid, oleic acid, stearic acid, linoleic acid, linolenic acid, benzoic acid, phthalic acid, isophthalic acid, terephthalic acid, salicylic acid, trifluoroacetic acid, monochloroacetic acid, dichloroacetic acid, trichloroacetic acid, oxalic acid, malonic acid, methylmalonic acid, ethylmalonic acid, propylmalonic acid, butylmalonic acid, dimethylmalonic acid, diethylmalonic acid, succinic acid, methylsuccinic acid, glutaric acid, adipic acid, itaconic acid, maleic acid, fumaric acid, citraconic acid, citric acid and the like. To maintain the stability, two or more acids may be used in combination.

The energy-sensitive composition according to the first aspect may include the above acid or not and, when including the acid, the amount of the acid used is usually 0.001% by mass or more and 10% by mass or less, and preferably 0.01% by mass or more and 5% by mass or less, based on the solid content (mass excluding a solvent) of the energy-sensitive composition.

A use ratio of the base generator (B) to the acid in the composition, for example, base generator (B):acid is 1:0.003 to 1:3.5, and preferably 1:0.01 to 1:3, in terms of a molar ratio. When the cation moiety is phosphazene, base generator (B):acid is more preferably 1:0.003 to 1:1 from the viewpoint of the stability of the composition. Regarding use of the base generator (B) and the acid, an adjustment may be made such that the pH of the energy-sensitive composition according to the first aspect is, for example, in a range of 4 or higher and 9 or lower, and preferably 5 or higher and 7 or lower.

<Solvent>

The composition according to the first aspect preferably includes a solvent. Examples of the solvent include cyclic skeleton-containing acetate compounds represented by the below-mentioned formula (S1), such as cycloalkyl acetate, alcohols such as methanol, ethanol, propanol and n-butanol; polyhydric alcohols such as ethylene glycol, diethylene glycol, propylene glycol and dipropylene glycol;

ketones such as acetone, methyl ethyl ketone, cyclohexanone, methyl-n-amyl ketone, methyl isoamyl ketone and 2-heptanone;

lactone ring-containing organic solvents such as γ-butyrolatone;

derivatives of polyhydric alcohols, for example, compounds having an ester bond, such as ethylene glycol monoacetate, diethylene glycol monoacetate, propylene glycol monoacetate or dipropylene glycol monoacetate, and compounds having an ether bond, such as monoalkyl ethers or monophenyl ethers, such as monomethyl ether, monoethyl ether, monopropyl ether and monobutyl ether of the polyhydric alcohols or the compounds having the ester bond;

cyclic ethers such as dioxane, and esters such as methyl lactate, ethyl lactate, methyl acetate, ethyl acetate, butyl acetate, methyl pyruvate, ethyl pyruvate, methyl methoxypropionate and ethyl ethoxypropionate;

aromatic organic solvents such as anisole, ethylbenzyl ether, cresyl methyl ether, diphenyl ether, dibenzyl ether, phenetole, butylphenyl ether, ethylbenzene, diethylbenzene, amylbenzene, isopropylbenzene, toluene, xylene, cymene and mesitylene;

nitrogen-containing organic solvents such as N,N,N',N'-tetramethylurea, N,N,2-trimethylpropionamide, N,N-dimethylacetamide, N,N-dimethylforamide, N,N-diethylacetamide, N,N-diethylformamide, 1,3-dimethyl-2-imidazolidinone, N-methylpyrrolidone and N-ethylpyrrolidone;
and the like.

Among these solvents, cycloalkyl acetate represented by the below-mentioned formula (S1), propylene glycol monomethyl ether acetate (PGMEA), propylene glycol monomethyl ether (PGME), N,N,N',N'-tetramethylurea (TMU) and butanol are preferable, cyclopropyl acetate, cyclobutyl acetate, cyclopentyl acetate, cyclohexyl acetate, cycloheptyl acetate or cyclooctyl acetate is more preferable, and cyclohexyl acetate is still more preferable. These solvents may be used alone or in combination of two or more.

[Chem. 16]

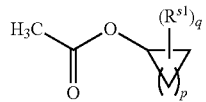

(S1)

In the formula (S1), $R^{s1}$ each independently represent an alkyl group, p is an integer of 1 or more and 6 or less, and q is an integer of 0 or more and (p+1) or less. Examples of the alkyl group represented by $R^{s1}$ include alkyl groups having 1 or more and 3 or less carbon atoms, and specific examples thereof include a methyl group, an ethyl group, an n-propyl group and an i-propyl group.

Specific examples of the cycloalkyl acetate represented by the formula (S1) include cyclopropyl acetate, cyclobutyl acetate, cyclopentyl acetate, cyclohexyl acetate, cycloheptyl acetate and cyclooctyl acetate. Among these, cyclooctyl acetate is preferable from the viewpoint of availability and the like. The cyclic skeleton-containing acetate compound may be used alone or in combination of two or more.

The content of the solvent in the energy-sensitive composition according to the first aspect is not particularly limited as long as it does not interfere with the object of the present invention. In view of film-forming properties, the solvent is used such that the solid component concentration of the energy-sensitive composition according to the first aspect is preferably 0.1% by mass or more and 50% by mass or less, and more preferably 1% by mass or more and 40% by mass or less. The solvent may be used alone or in combination of two or more.

(Other Components)

The energy-sensitive composition according to the first aspect may include, as the stabilizer, a monohydric or dihydric or higher polyhydric alcohol which has a cyclic ether as a substituent, or an ether compound. Specific examples of usable stabilizer include stabilizers mentioned in Japanese Unexamined Patent Application, Publication No. 2009-126940, paragraphs (0180) to (0184).

The energy-sensitive composition according to the first aspect may include water. The addition of water leads to an improvement in lithographic performance. The content of water in a solvent component of the energy-sensitive composition according to the first aspect is, for example, 0% by mass or more and less than 50% by mass, and preferably 0.5% by mass or more and 5% by mass or less.

The energy-sensitive composition according to the first aspect may optionally include a surfactant. Specific examples of usable surfactant include surfactants mentioned in Japanese Unexamined Patent Application, Publication No. 2009-126940, paragraph (0185).

<Applications>

The energy-sensitive composition according to the first aspect can be used in applications for formation of a protective film or an interlayer film which protects various substrates (including a metal oxide-containing film, various metals-containing films). Examples of various substrates include substrates for display materials (including a metal oxide-containing film, a film containing various metals) such as a semiconductor substrate, a liquid crystal display, an organic light-emitting display (OLED), an electrophoretic display (electronic paper), a touch panel, a color filter, and a back light; substrates for solar cells; substrates for photoelectric conversion elements (including a metal oxide-containing film, a film containing various metals) such as an optical sensor; and substrates for photoelectric elements (including a metal oxide-containing film, a film containing various metals).

<<Cured Product>>

The cured product according to the second aspect is a cured product of the energy-sensitive composition according to the first aspect. When the cured product is a film, the thickness is preferably 10 nm or more and 10,000 nm or less, more preferably 50 nm or more and 5,000 nm or less, and still more preferably 100 nm or more and 3,000 nm or less. Since the energy-sensitive composition according to the first aspect is excellent in curability, when the cured product is a film, a residual film ratio after the below-mentioned development (for example, development with a solvent) is preferably 50% or more, more preferably 55% or more, still more preferably 60% or more, particularly preferably 65% or more, and most preferably 70% or more. Preferred range of the residual film ratio is preferred range of a residual film ratio determined in accordance with an evaluation method in "evaluation of curability (residual film ratio)" mentioned below in Examples. The cured product is suitable for various applications, for example, sealing material for OLED display element, OLED lightings, hard coats, insulating films, antireflective films, interlayer insulating films, carbon hard masks, display panel materials (flattened films, pixels for color filter, barrier ribs for organic EL, spacers) and the like. The cured product is preferably used as a transparent coating film for covering a metal wiring in display elements such as touch panel.

<<Pattern Forming Method>>

The pattern forming method according to the third aspect includes applying the energy-sensitive composition according to the first aspect onto a substrate to form a film, and exposing the film. The method of forming a film using the energy-sensitive composition according to the first aspect is not particularly limited as long as the effects of the present invention are not impaired, and includes a method of applying the energy-sensitive composition onto an optional support, using optionally contact transfer coating applicators such as a roll coater, a reverse coater, a bar coater and an inkjet; and on-contact applicators such as a spinner (rotary applicator) and a curtain flow coater. Examples of the substrate include, but are not limited to, a glass substrate, a quartz substrate, a transparent or translucent resin substrate (for example, heat-resistant materials such as polycarbonate, polyethylene terephthalate, polyether sulfone, polyimide, and polyamideimide), metal, a silicon substrate and the like. The substrate may be various substrates, for example, substrates for display materials (including a metal oxide-containing film, a film containing various metals) such as a semiconductor substrate, a liquid crystal display, an organic light-emitting display (OLED), an electrophoretic display (electronic paper), a touch panel, a color filter, and a back light; substrates for solar cells; substrates for photoelectric conversion elements (including a metal oxide-containing film, a film containing various metals) such as an optical sensor; and substrates for photoelectric devices (including a metal oxide-containing film, a film containing various metals). The thickness of the substrate is not particularly limited and can be appropriately selected according to embodiment of usage of a pattern forming material.

After application, the coating film is preferably dried (prebaked). The drying method is not particularly limited and includes, for example, (1) a method of drying with a hot plate at a temperature of 80° C. or higher and 180° C. or lower, and preferably 90° C. or higher and 160° C. or lower, for 60 seconds or more and 120 seconds or less, (2) a method of allowing to stand at room temperature for several hours to several days, (3) a method of placing in a hot-air heater or an infrared heater for several tens of minutes to several hours to remove the solvent and the like.

After drying, the coating film may be exposed by irradiating with radiation. Examples of radiation include active energy rays such as ultraviolet rays and excimer laser beams, and examples of a light source of the radiation include light sources emitting ultraviolet rays, such as a high pressure mercury lamp, an ultra-high pressure mercury lamp, a xenon lamp and a carbon arc lamp. The irradiation dose is not particularly limited and is, for example, 30 mJ/cm$^2$ or more and 2,000 mJ/cm$^2$ or less. The exposure step may be performed in place of or together with the below-mentioned baking step. In the exposure step, for example, the thus formed coating film may be selectively exposed and, when including the selective exposure step, the developing step may also be included. For example, the thus formed coating film may be subjected to imprint lithography. When imprint lithography is formed, there is exemplified, for example, a method including the steps of: applying the energy-sensitive composition according to the first aspect onto a substrate to form a coating film, pressing a mold, on which an irregular structure of a predetermined pattern is formed, against the coating film, and performing exposure. The exposure step is performed against the coating film composed of the energy-sensitive composition according to the first aspect in a state where the mold is pressed against the coating film. After curing by exposure, the mold is peeled off, thus making it possible to form a pattern according to a shape of the mold.

After exposure, a pattern having a satisfactory shape can be formed without heating (PEB), and the exposed film may be subjected to PEB. PEB is performed, for example, at 80° C. or higher and 180° C. or lower for 30 seconds or more and 120 seconds or less. As mentioned above, when including a selective exposure step, the film is preferably developed to form a pattern after exposure. The development can be performed using an alkali developing solution or a developing solution containing an organic solvent, and it is more preferable that the development is performed using a developing solution containing an organic solvent. Examples of the organic solvent contained in the developing solution include those which are the same as specific examples and preferred examples of the <solvent> in the composition according to the first aspect.

After drying, exposure, or development, the coating film is preferably baked (post-baked) in view of enhancing film physical properties. The baking temperature is, for example, in a range of 200° C. or higher and 1,000° C. or lower, and preferably 230° C. or higher and 700° C. or lower, in view of an improvement in pencil hardness and an enhancement in permanent film properties or a decrease in dielectric constant, although it depends on a lower layer substrate and embodiment of usage. More preferably, the baking temperature may be appropriately adjusted in a range of 250° C. or higher and 600° C. or lower. The baking atmosphere is not particularly limited and may be an inert gas atmosphere such as a nitrogen atmosphere or argon atmosphere, or may be under vacuum or reduced pressure. The baking atmosphere may be under the atmosphere, or the oxygen concentration may be appropriately controlled. The baking time may be appropriately changed, and is 10 minutes or more and 120 minutes or less.

The thickness of the film formed by the method according to the third aspect is preferably 10 nm or more and 10,000 nm or less, more preferably 50 nm or more and 5,000 nm or less, and still more preferably 100 nm or more and 3,000 nm or less.

Examples

The present invention will be described in more detail by way of Examples, but the present invention is not limited to these Examples.

[Synthesis Example 1] Synthesis of Polysilane Compound 1

Using diphenyldichlorosilane as a raw material, polydiphenylsilane (Mw of 2,600) was produced in accordance with the method mentioned in JACS, 110, 124 (1998) and Macromolecules, 23, 3423 (1990) and used as a polysilane compound 1 in the following respective Examples and Comparative Example 1.

[Synthesis Example 2] Synthesis of Polysilane Compound 2

In a round-bottom flask having an internal volume of 1,000 ml equipped with a three-way cock, 43.45 g of granular (particle diameter of 20 to 1,000 μm) magnesium, 5.26 g of tris(acetylacetonato)iron (III) as a catalyst and 1.26 g of anhydrous lithium chloride were charged. After drying the interior of the reactor (flask) by heating at 50° C. under reduced pressure of 1 mmHg (=133 kPa), a dry argon gas was introduced into the reactor and 132.13 ml of tetrahydrofuran (THF) dried in advance with sodium-benzophenone ketyl, followed by stirring at 25° C. for about 60 minutes. To this reaction mixture, 42.0 g (0.3 mol) of methyl vinyl dichlorosilane purified in advance by distillation was added using a syringe, followed by stirring at 25° C. for about 12 hours. After completion of the reaction, 1,000 ml of 1N (=1M/L) hydrochloric acid was added to the reaction mixture and extraction was performed with 500 ml of toluene. The toluene phase was washed ten times with 200 ml of pure water and dried over anhydrous magnesium sulfate, and then toluene was distilled off to obtain a methyl vinyl silane polymer (mass average molecular weight: 1900). The thus-obtained polymer was used as a polysilane compound 2 in Examples 6 to 7.

Compounds (b1) to (b5) and (cb) represented by the following formulas were produced and used, as base generators, in each of the following Examples and Comparative Example 1. The pKa of the cation moiety of each compound is as follows.
(b1): pKa=33
(b2): pKa=43
(b3): pKa=43
(b4): pKa=24.3
(b5): pKa=32.9
(cb): pKa=23.4

[Chem. 17]

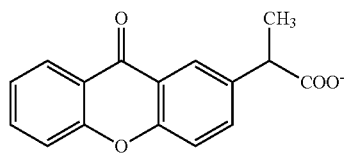
(b1)

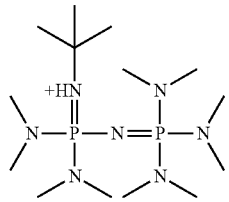

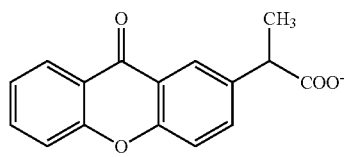
(b2)

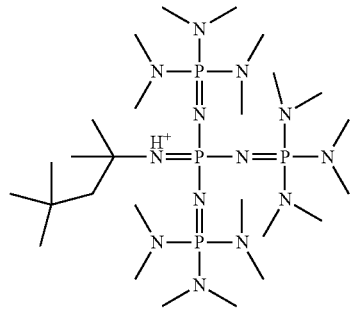

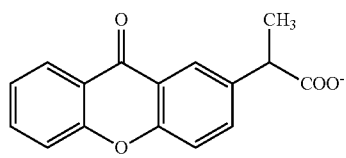
(b3)

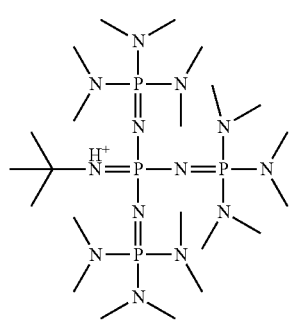

[Chem. 18]

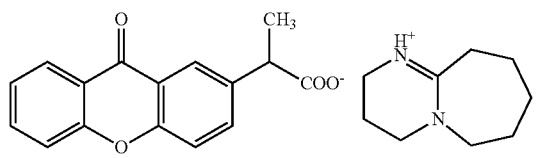
(b4)

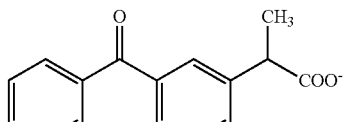
(b5)

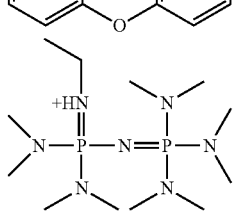

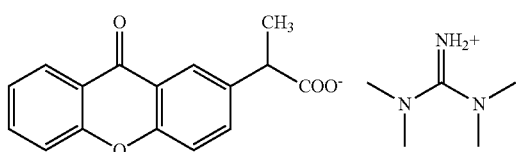
(cb)

[Examples 1 to 5 and Comparative Example 1]
Preparation of Energy-Sensitive Composition In cyclohexyl acetate, 27.6% by mass of the above polysilane compound 1 was dissolved such that the solid component concentration became 30% and 2.4% by mass of a base generator shown in Table 1 was dissolved, followed by filtration through a filter having a pore size of 0.1 μm made of a fluororesin to prepare energy-sensitive compositions of the respective Examples and Comparative Example 1.

[Example 6] Preparation of Energy-Sensitive Composition

In cyclohexyl acetate, 27.6% by mass of the polysilane compound 2 was dissolved such that the solid component concentration became 30% and 2.4% by mass of a compound (b1) as a base generator was dissolved, followed by filtration through a filter having a pore size of 0.1 μm made of a fluororesin to prepare an energy-sensitive composition of Example 6.

[Example 7] Preparation of Energy-Sensitive Composition

In cyclohexyl acetate, 27.6% by mass of the polysilane compound 2 was dissolved such that the solid component concentration became 30% and 2.4% by mass of a compound (b5) as a base generator was dissolved, followed by filtration through a filter having a pore size of 0.1 μm made of a fluororesin to prepare an energy-sensitive composition of Example 7.

[Evaluation of Curability (Residual Film Ratio)]

Using a spin coater, each of the energy-sensitive compositions of the respective Examples and Comparative Example 1 was applied onto a wafer to form a coating film having a thickness of 3 μm. The coating film was baked at 140° C. for 30 seconds to obtain a cured coating film. The cured coating film thus obtained was subjected to a developing treatment with a solvent (cyclohexyl acetate) by a dipping method for 60 seconds. Using a profilometer (trade name: Dektak 3ST, manufactured by ULVAC, Inc.), the thickness of the cured coating film after dipping in the solvent was measured. A residual film ratio, which is a ratio of the thickness before and after the development, was measured. The results are shown in Table 1.

TABLE 1

|  | Base generator | Residual film ratio |
|---|---|---|
| Example 1 | (b1) | 100% |
| Example 2 | (b2) | 67% |
| Example 3 | (b3) | 55% |
| Example 4 | (b4) | 63% |
| Example 5 | (b5) | 95% |
| Comparative Example 1 | (cb) | 0% |

As is apparent from the results shown in Table 1, Comparative Example 1 in which a pKa of the base constituting a counter cation in a base generator is less than 24 is inferior in curability since a residual film ratio after the development is 0%. Meanwhile, all of Examples 1 to 4 in which a pKa of the base constituting a counter cation in a base generator is 24 or more are excellent in curability since a residual film ratio after the development is 55% or more.

[Patterning Evaluation 1]

With respect to the energy-sensitive compositions of Example 1, Example 4 and Example 5, patterning was evaluated. Using a spin coater, each of the energy-sensitive compositions of Example 1 and Example 5 was applied onto a wafer to form a coating film having a thickness of 3 µm. The coating film was subjected to regioselective broadband exposure at 250 mJ/cm² by an ultraviolet aligner using a mask having a line width of 4 µm and a line-and-space of 1:1. The exposed coating film was baked at 160° C. for 30 seconds to obtain a cured coating film. The cured coating film thus obtained was subjected to a developing treatment with a solvent (cyclohexyl acetate) by a dipping method for 60 seconds. As a result, patterns having a line width of 4 µm and a line-and-space of 1:1 and having excellent contrast between the exposed portions and the unexposed portions were obtained from the energy-sensitive compositions of all of Examples.

In the same manner as in patterning of the energy-sensitive composition of Example 1, except that the line width of the mask was changed from 4 µm to 100 µm, patterning of the energy-sensitive composition of Example 4 was performed. As a result, patterns having a line width of 100 µm and a line-and-space of 1:1 and having excellent contrast between the exposed portions and the unexposed portions were obtained. Each of patterns obtained by the above-mentioned Patterning Evaluation 1 was pre-baked at 230° C. and, as a result, patterns having satisfactory permanent film properties could be obtained.

[Patterning Evaluation 2]

With respect to the energy-sensitive compositions of Example 6 and Example 7, patterning was evaluated. Using a spin coater, each of the energy-sensitive compositions of Example 6 and Example 7 was applied onto a wafer to form a coating film having a thickness of 3 µm. The coating film was subjected to regioselective broadband exposure at 250 mJ/cm² by an ultraviolet aligner using a mask having a line width of 4 µm and a line-and-space of 1:1. The exposed coating film was baked at 160° C. for 30 second to obtain a cured coating film. The cured coating film thus obtained was subjected to a developing treatment with a solvent (acetone) by a dipping method for 60 seconds. As a result, patterns having a line width of 4 µm and a line-and-space of 1:1 and having excellent contrast between the exposed portions and the unexposed portions were obtained from the energy-sensitive compositions of all of Examples. Each of patterns obtained by the above-mentioned Patterning Evaluation 2 was pre-baked at 230° C. and, as a result, patterns having satisfactory permanent film properties could be obtained.

What is claimed is:

1. An energy-sensitive composition comprising: at least one silane compound (A) selected from the group consisting of a silane compound monomer capable of forming a polysilane compound, a silane compound oligomer, and the polysilane compound;

an acid; and a base generator (B) represented by the following formula (1):

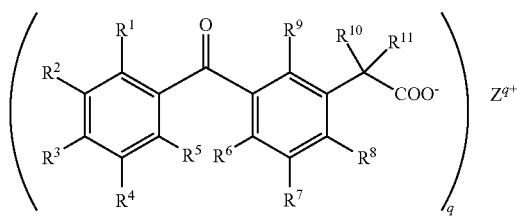

wherein, in the above formula, $R^1$ to $R^{11}$ each independently represents a hydrogen atom, a halogen atom, a nitro group, an alkyl group, an aryl group, an arylalkyl group or an alkoxy group, $R^5$ and $R^6$ may be connected to each other via a single bond or a divalent linking group, $Z^{q+}$ represents a q-valent counter cation composed of a base having a pKa of 24 or more, and q represents an integer of 1 or more, and wherein a content ratio of the base generator (B) to the acid in the composition is base generator (B):acid=1: 0.003 to 1:3.5 in terms of a molar ratio.

2. The energy-sensitive composition according to claim 1, wherein the counter cation includes at least one cation selected from the group consisting of a phosphazene compound cation and an amidine compound cation.

3. The energy-sensitive composition according to claim 2, wherein a phosphazene compound comprising the phosphazene compound cation is a compound represented by the following formula (b1) or a compound in which at least two structures represented by the following formula (b1) are connected to each other, and an amidine compound constituting the amidine compound cation is a compound represented by the following formula (b2):

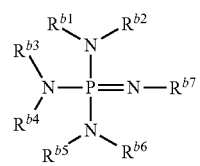

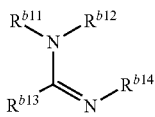
(b2)

wherein, in the above formula (b1), $R^{b1}$ to $R^{b7}$ each independently represents a monovalent organic group which may include a hydrogen or hetero atom, and at least two of $R^{b1}$ to $R^{b7}$ may be bonded to each other to form a ring, and wherein, in the above formula (b2), $R^{b11}$ to $R^{b14}$ each independently represents a monovalent organic group which may include a hydrogen or hetero atom, at least one of $R^{b11}$ to $R^{b14}$ represents a monovalent organic group which may include a hetero atom, and at least two of $R^{b11}$ to $R^{b14}$ may be bonded to each other to form a ring.

4. The energy-sensitive composition according to claim 1, wherein the silane compound monomer is a compound represented by the following formula (a):

$$X_{n1}SiR_{4-n1} \quad (a)$$

wherein n1 is an integer of 2 or more and 4 or less, n1X(s) are each independently a halogen atom, and (4−n1)R(s) are each independently a hydrogen atom, a hydroxyl group, an organic group or a silyl group.

5. A cured product of the energy-sensitive composition according to claim 1.

6. A pattern forming method comprising applying the energy-sensitive composition according to claim 1 onto a substrate to form a film, and exposing the film.

7. The pattern forming method according to claim 6, further comprising developing to form a pattern after exposing the film.

8. The energy-sensitive composition according to claim 1, wherein the acid is an acid represented by the following formula (K):

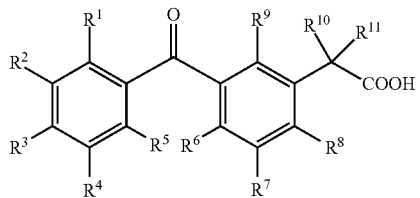

wherein, in the above formula, $R^1$ to $R^{11}$ are synonymous with $R^1$ to $R^{11}$ in formula (1).

9. The energy-sensitive composition according to claim 1, wherein the content ratio of the base generator (B) to the acid in the composition is base generator (B):acid=1: 0.003 to 1:1 in terms of a molar ratio, and wherein the counter cation is a phosphazene compound cation.

10. The energy-sensitive composition according to claim 1, wherein the silane compound (A) is at least one selected from the group consisting of a silane compound monomer capable of forming a polysilane compound, a silane compound oligomer in which at least two of the silane compound monomers are polymerized, and a polysilane compound in which the silane compound monomer is polymerized, and the silane compound monomer is a compound represented by the following formula (a):

$$X_{n1}SiR_{4-n1} \quad (a)$$

wherein n1 is an integer of 2 or more and 4 or less, n1X(s) are each independently a halogen atom, (4−n1)R(s) are each independently a hydrogen atom, a hydroxyl group, an organic group or a silyl group, and at least one of the (4−n1)R(s) is a vinyl group.

* * * * *